US012745987B2

(12) United States Patent
Wang et al.

(10) Patent No.: US 12,745,987 B2
(45) Date of Patent: Sep. 29, 2026

(54) SYSTEMS AND METHODS FOR ADAPTIVE CONTRAST-ENHANCED ULTRASOUND IMAGING

(71) Applicant: KONINKLIJKE PHILIPS N.V., Eindhoven (NL)

(72) Inventors: Shiying Wang, Melrose, MA (US); Thanasis Loupas, Kirkland, MA (US); Jeffry Earl Powers, Bainbridge Island, WA (US); Claudia Errico, Cambridge, MA (US); William Tao Shi, Wakefield, MA (US); Paul Sheeran, Woodinville, WA (US); Charles Tremblay-Darveau, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 530 days.

(21) Appl. No.: 17/777,891

(22) PCT Filed: Nov. 18, 2020

(86) PCT No.: PCT/EP2020/082512
§ 371 (c)(1),
(2) Date: May 18, 2022

(87) PCT Pub. No.: WO2021/099372
PCT Pub. Date: May 27, 2021

(65) Prior Publication Data

US 2022/0409182 A1 Dec. 29, 2022

Related U.S. Application Data

(60) Provisional application No. 62/938,554, filed on Nov. 21, 2019.

(51) Int. Cl.
*A61B 8/00* (2006.01)

(52) U.S. Cl.
CPC .............. *A61B 8/5207* (2013.01); *A61B 8/48* (2013.01); *G06T 2207/10132* (2013.01)

(58) Field of Classification Search
CPC ......... A61B 8/48; A61B 8/481; A61B 8/5207; A61B 8/5253; A61B 8/5269;
(Continued)

(56) References Cited

U.S. PATENT DOCUMENTS 6,443,896 B1 9/2002 Detmer
6,530,885 B1 3/2003 Entrekin et al.
(Continued)

FOREIGN PATENT DOCUMENTS

WO 2020141127 A1 7/2020

OTHER PUBLICATIONS

M. Kahiralseed et al., "Contrast-enhanced ultrasound imaging using pulse inversion spectral deconvolution," 2019, The Journal of the Acoustical Society of America, 146, pp. 2466-2474 (Year: 2019).*
(Continued)

*Primary Examiner* — Michael J Carey
*Assistant Examiner* — Maria Christina Talty

(57) ABSTRACT

Systems and methods for generating adaptive contrast accumulation imaging images are disclosed. A point spread function thinning/skeletonization technique may be performed on contrast enhanced image frames. An aggressiveness parameter of the technique may be adapted temporally and/or spatially. The aggressiveness parameter may be adapted based on various factors, including, but not limited to, time since injection of the contrast agent, signal intensity, and/or vessel size. The images may be temporally accumulated to generate a final sequence of adaptive contrast accumulation imaging images.

23 Claims, 9 Drawing Sheets

(58) Field of Classification Search
CPC ............... A61B 8/5276; G01S 15/8915; G01S 15/8977; G01S 7/52039; G06T 2207/10132
See application file for complete search history.

(56) References Cited

U.S. PATENT DOCUMENTS

| | | | | |
|---|---|---|---|---|
| 2009/0299184 | A1* | 12/2009 | Walker | G10K 11/346<br>600/447 |
| 2019/0192229 | A1* | 6/2019 | Berlin | A61B 8/5246 |
| 2019/0254637 | A1* | 8/2019 | Sabata | A61B 8/5223 |
| 2019/0365355 | A1* | 12/2019 | Eldar | A61B 8/488 |

OTHER PUBLICATIONS

International Search Report and Written Opinion for PCT/EP2020/082512; Mailing date: Feb. 19, 2021; 10 pages.

Maragos, P.; "Morphological Filtering for Image Enhancement and Feature Detection", The Image and Video Processing Handbook, 2nd Ed., 2005, Chapter 3.3, pp. 135-156.

Soille, P.; "Morphological Operators", Computer Vision and Applications: A Guide for Students and Practitioners, 2000, 34 pages.

Bar-Zion A. et al., "Fast Vascular Ultrasound Imaging With Enhanced Spatial Resolution and Background Rejection", IEEE Trans Med Imaging, 2017; vol. 36, No. 1, pp. 169-180.

Dertinger T. et al., "Fast, background-free, 3D super-resolution optical fluctuation imaging (SOFI)", Proc Natl Acad Sci, 2009, vol. 106, No. 52, pp. 22287-22292.

Jia, S. et al., "Isotropic three-dimensional super-resolution imaging with a self-bending point spread function", Nature Photonics, 2014, vol. 8, pp. 302-306.

Izeddin I., et al., "PSF shaping using adaptive optics for three-dimensional single-molecule super-resolution imaging and tracking," Opt. Express, 2012, vol. 20, pp. 4957-4967.

* cited by examiner

102

100

SYSTEMS AND METHODS FOR ADAPTIVE CONTRAST-ENHANCED ULTRASOUND IMAGING

CROSS-REFERENCE TO PRIOR APPLICATIONS

This application is the U.S. National Phase application under 35 U.S.C. § 371 of International Application No. PCT/EP2020/082512, filed on Nov. 18, 2020, which claims the benefit of U.S. Provisional Patent Application No. 62/938,554, filed on Nov. 21, 2019. These applications are hereby incorporated by reference herein.

TECHNICAL FIELD

This application relates to contrast enhanced imaging. More specifically, this application relates to generating contrast accumulation images.

BACKGROUND

In contrast-enhanced imaging, a contrast agent is provided to an area or volume to be imaged in order to provide a higher signal strength from the area or volume, or selectively enhance signals from areas or volumes with high contrast concentration. For example, in contrast-enhanced ultrasound (CEUS), microbubbles may be injected into a subject's bloodstream and ultrasound images may be acquired of the subject's vasculature. Without the microbubbles, little to no signal may be provided by the blood vessels. In contrast accumulation imaging (CAI), multiple contrast-enhanced images (e.g., multiple image frames) are acquired and combined to form the final image, which can be used to map contrast agent progression and enhance vessel topology and conspicuity. This temporal accumulation imaging of CEUS has been commercialized and widely used for vascularity visualization.

SUMMARY

Systems and methods for an adaptive contrast-enhanced ultrasound technique that replaces microbubble identification and localization steps in contrast accumulation image processing with an adaptive point spread function (PSF) thinning/skeletonization technique (e.g., thinning technique). The PSF size may be adaptive both spatially (e.g., to blood vessel size) and temporally (e.g., to different perfusion times) based, at least in part, by adapting an aggressiveness parameter. This may provide enhanced vascular imaging performance for both large branches and microvessels at different contrast perfusion phases with reduced processing requirements.

In some examples, a contrast infused tissue image loop may be acquired. The adaptive PSF thinning technique may be applied to each frame of the contrast loop, in which the size of the PSF may be adaptive based on spatial regions within the image and/or adaptive over time. After adaptive PSF thinning technique is performed, a temporal accumulation of the contrast image frames to achieve high resolution may be performed. In some examples, the temporal accumulation may use a maximum intensity each frame at each pixel or show average intensity at each pixel.

In accordance with at least one example disclosed herein, an ultrasound system may include an ultrasound probe for receiving ultrasound signals for a plurality of transmit/receive events, and at least one processor in communication with the ultrasound probe, the at least one processor configured to perform an adaptive thinning technique on the ultrasound signals for the plurality of transmit/receive events, wherein the adaptive thinning technique is based, at least in part, on an aggressiveness parameter that is adapted in at least one of a temporal domain or a spatial domain and temporally accumulate the ultrasound signals for the plurality of transmit/receive events on which the adaptive thinning technique is performed to generate an adaptive contrast accumulation image.

In accordance with at least one example disclosed herein, a method may include receiving a plurality of contrast enhanced ultrasound images performing an adaptive thinning technique on individual ones of the plurality of contrast enhanced ultrasound images, wherein the adaptive thinning technique is based, at least in part, on an aggressiveness parameter that is adapted in at least one of a temporal domain or a spatial domain, and temporally accumulating at least two of the individual ones of the plurality of ultrasound images to provide an adaptive contrast accumulation image.

In accordance with at least one example disclosure herein, a non-transitory computer readable medium may include instructions that when executed cause an ultrasound imaging system to receive a plurality of contrast enhanced ultrasound images, perform an adaptive thinning technique on individual ones of the plurality of contrast enhanced ultrasound images, wherein the adaptive thinning technique is based, at least in part, on an aggressiveness parameter that is adapted in at least one of a temporal domain or a spatial domain, and temporally accumulate at least two of the individual ones of the plurality of ultrasound images to provide an adaptive contrast accumulation image.

DESCRIPTION

The following description of certain exemplary examples is merely exemplary in nature and is in no way intended to limit the invention or its applications or uses. In the following detailed description of examples of the present systems and methods, reference is made to the accompanying drawings which form a part hereof, and in which are shown by way of illustration specific examples in which the described systems and methods may be practiced. These examples are described in sufficient detail to enable those skilled in the art to practice the presently disclosed systems and methods, and it is to be understood that other examples may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Accumulation CEUS may have limited spatial resolution due to the large size of the point spread function (PSF) in contrast mode. The PSF is a measure of blurring or spreading of a point source by an imaging system. To improve the spatial resolution, image processing techniques, such as super resolution imaging (SRI) may be performed. In SRI, individual microbubbles are identified and represented as single pixels (e.g., localized). However, the number of images required to be accumulated to generate an SRI image may be significant. Furthermore, the processing time and/or power necessary for the identification and localization of the microbubbles may also be prohibitive, especially if real-time or near real-time visualization is desired.

Another issue in CEUS imaging is that there may be a wide distribution of vessel size in an image. While traditional accumulation CEUS may be sufficient for larger vessels, visualization of smaller vessels may benefit more from other techniques such as SRI. Similarly, in a series of images, there may be a wide distribution in contrast agent concentration over time. Applying a single image processing technique may lead to enhanced visualization of only one vessel type and/or enhanced visualization only for a particular time period (e.g., early perfusion phase, late accumulation phase) of the contrast imaging scan.

Figure 1:
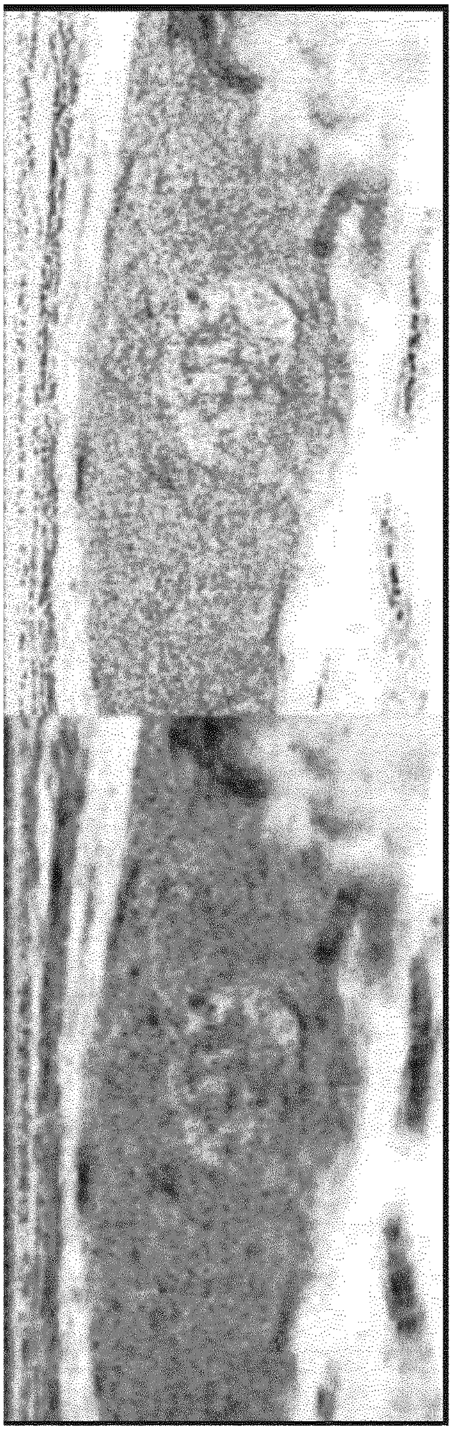
FIG. 1 shows two example contrast accumulation images acquired by two different image processing techniques.

FIG. 1 shows two example contrast accumulation images acquired by two different image processing techniques. Both image 100 and image 102 were acquired from a human thyroid at the early perfusion phase of CEUS. Image 100 was generated using typical contrast accumulation imaging (CAI) techniques. Image 100 shows good sensitivity to the contrast agent, but its spatial resolution is limited and areas show signs of saturation. Image 102 was acquired using an enhanced CAI technique as described in U.S. Provisional Application No. 62/787,860 filed on Jan. 3, 2019. Image 102 shows better spatial resolution than image 100, but it is discontinuous and less sensitive to contrast agent signals than the typical CAI technique. Thus, while image 102 illustrates an advance in the art which may allow greater spatial resolution and/or improved visualization of smaller vasculature with fewer frames than SRI, adaptive CAI techniques that can provide improved visualization of both larger and smaller vasculature over time is desired. Furthermore, adaptive techniques that do not require microbubble identification and localization (such as in SRI), may be desirable to reduce processing time and/or power.

The present disclosure is directed to systems and methods for performing image processing techniques that are spatially and temporally adaptive. The techniques described herein may be referred to as "adaptive CAI." These techniques may adapt an aggressiveness parameter of a PSF thinning/skeletonization technique to provide better visualization of both large and small vessels and over all phases of a contrast enhanced imaging scan.

Figure 2:
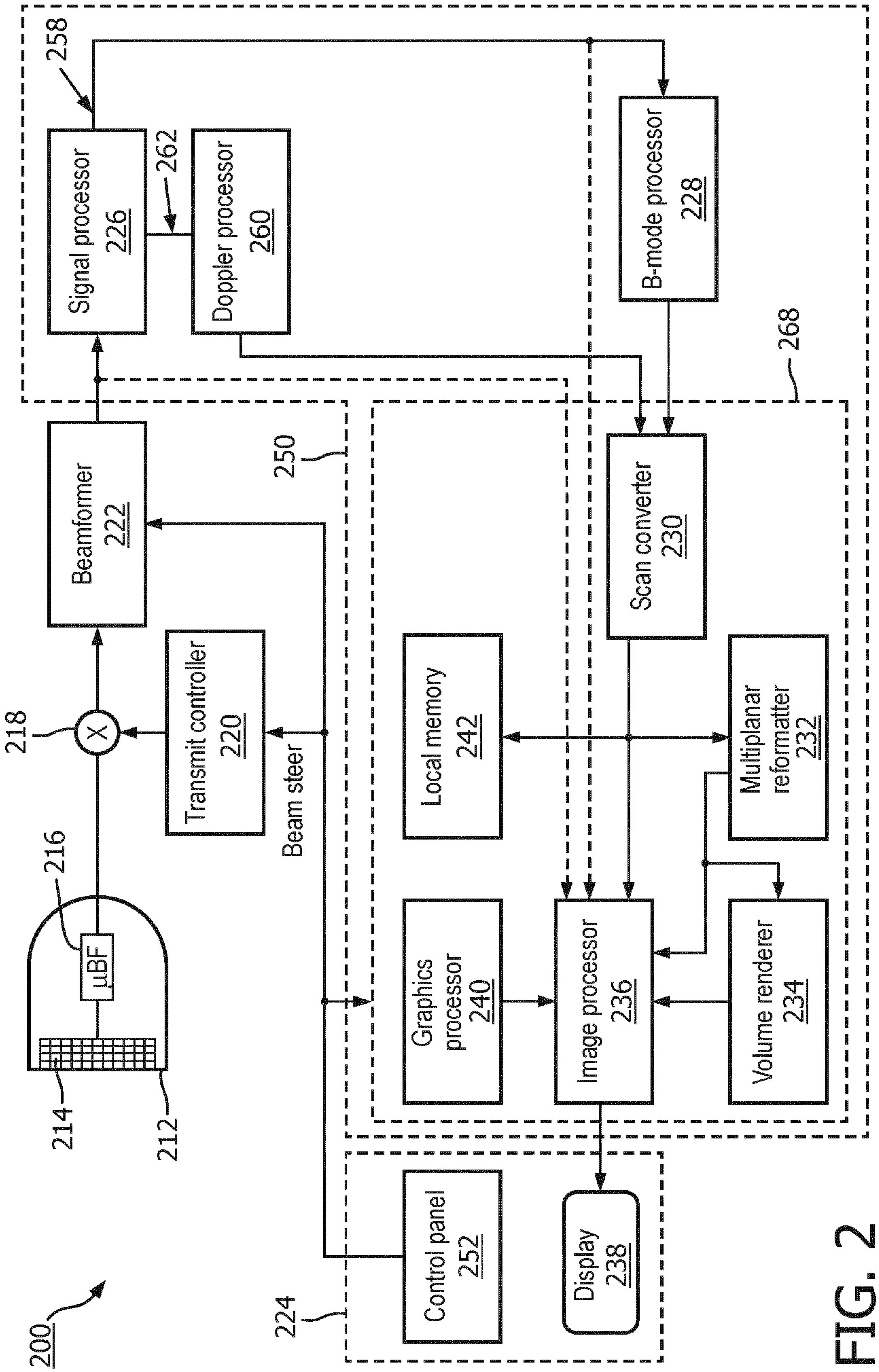
FIG. 2 is a block diagram of an ultrasound imaging system arranged in accordance with some examples of the present disclosure.

FIG. 2 shows a block diagram of an ultrasound imaging system 200 constructed in accordance with the principles of the present disclosure. An ultrasound imaging system 200 according to the present disclosure may include a transducer array 214, which may be included in an ultrasound probe 212, for example an external probe or an internal probe such as an intravascular ultrasound (IVUS) catheter probe. In other examples, the transducer array 214 may be in the form of a flexible array configured to be conformally applied to a surface of subject to be imaged (e.g., patient). The transducer array 214 is configured to transmit ultrasound signals (e.g., beams, waves) and receive echoes (e.g., received ultrasound signals) responsive to the transmitted ultrasound signals. A variety of transducer arrays may be used, e.g., linear arrays, curved arrays, or phased arrays. The transducer array 214, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

In some examples, the transducer array 214 may be coupled to a microbeamformer 216, which may be located in the ultrasound probe 212, and which may control the transmission and reception of signals by the transducer elements in the array 214. In some examples, the microbeamformer 216 may control the transmission and reception of signals by active elements in the array 214 (e.g., an active subset of elements of the array that define the active aperture at any given time).

In some examples, the microbeamformer 216 may be coupled, e.g., by a probe cable or wirelessly, to a transmit/receive (T/R) switch 218, which switches between transmission and reception and protects the main beamformer 222 from high energy transmit signals. In some examples, for example in portable ultrasound systems, the T/R switch 218 and other elements in the system can be included in the ultrasound probe 212 rather than in the ultrasound system base, which may house the image processing electronics. An ultrasound system base typically includes software and hardware components including circuitry for signal processing and image data generation as well as executable instructions for providing a user interface.

The transmission of ultrasonic signals from the transducer array 214 under control of the microbeamformer 216 is directed by the transmit controller 220, which may be coupled to the T/R switch 218 and a main beamformer 222. The transmit controller 220 may control the direction in which beams are steered. Beams may be steered straight ahead from (orthogonal to) the transducer array 214, or at different angles for a wider field of view. The transmit controller 220 may also be coupled to a user interface 224 and receive input from the user's operation of a user control. The user interface 224 may include one or more input devices such as a control panel 252, which may include one or more mechanical controls (e.g., buttons, encoders, etc.), touch sensitive controls (e.g., a trackpad, a touchscreen, or the like), and/or other known input devices.

In some examples, the partially beamformed signals produced by the microbeamformer 216 may be coupled to a main beamformer 222 where partially beamformed signals from individual patches of transducer elements may be combined into a fully beamformed signal. In some examples, microbeamformer 216 is omitted, and the transducer array 214 is under the control of the beamformer 222 and beamformer 222 performs all beamforming of signals. In examples with and without the microbeamformer 216, the beamformed signals of beamformer 222 are coupled to processing circuitry 250, which may include one or more processors (e.g., a signal processor 226, a B-mode processor 228, a Doppler processor 260, and one or more image generation and processing components 268) configured to produce an ultrasound image from the beamformed signals (i.e., beamformed RF data).

The signal processor 226 may be configured to process the received beamformed RF data in various ways, such as bandpass filtering, decimation, I and Q component separation, and harmonic signal separation. The signal processor 226 may also perform additional signal enhancement such as speckle reduction, signal compounding, and electronic noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 258 which couples the signals from the signal processor 226 to a B-mode processor 228 for producing B-mode image data.

The B-mode processor 228 can employ amplitude detection for the imaging of structures in the body. According to principles of the present disclosure, the B-mode processor 228 may generate signals for tissue images and/or contrast images. In some embodiments, signals from the microbubbles may be extracted from the B-mode signal for forming a separate contrast image. Similarly, the tissue signals may be separated from the microbubble signals for generating a tissue image. The signals produced by the B-mode processor 228 may be coupled to a scan converter 230 and/or a multiplanar reformatter 232. The scan converter 230 may be configured to arrange the echo signals from the spatial relationship in which they were received to a desired image format. For instance, the scan converter 230 may arrange the echo signal into a two dimensional (2D) sector-shaped format, or a pyramidal or otherwise shaped three dimensional (3D) format. In another example of the present disclosure, the scan converter 230 may arrange the echo signals into side-by-side contrast enhanced and tissue images.

The multiplanar reformatter 232 can convert echoes which are received from points in a common plane in a volumetric region of the body into an ultrasonic image (e.g., a B-mode image) of that plane, for example as described in U.S. Pat. No. 6,443,896 (Detmer). The scan converter 230 and multiplanar reformatter 232 may be implemented as one or more processors in some examples.

A volume renderer 234 may generate an image (also referred to as a projection, render, or rendering) of the 3D dataset as viewed from a given reference point, e.g., as described in U.S. Pat. No. 6,530,885 (Entrekin et al.). The volume renderer 234 may be implemented as one or more processors in some examples. The volume renderer 234 may generate a render, such as a positive render or a negative render, by any known or future known technique such as surface rendering and maximum intensity rendering.

In some examples, the system may include a Doppler signal path 262 which couples the output from the signal processor 226 to a Doppler processor 260. The Doppler processor 260 may be configured to estimate the Doppler shift and generate Doppler image data. The Doppler image data may include color data which is then overlaid with B-mode (i.e. grayscale) image data for display. The Doppler processor 260 may be configured to filter out unwanted signals (i.e., noise or clutter associated with non-moving tissue), for example using a wall filter. The Doppler processor 260 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo further threshold detection to further reduce noise, as well as segmentation and post-processing such as filling and smoothing. The velocity and power estimates may then be mapped to a desired range of display colors in accordance with a color map. The color data, also referred to as Doppler image data, may then be coupled to the scan converter 230, where the Doppler image data may be converted to the desired image format and overlaid on the B-mode image of the tissue structure to form a color Doppler or a power Doppler image. For example, Doppler image data may be overlaid on a B-mode image of the tissue structure.

Output (e.g., B-mode images, Doppler images) from the scan converter 230, the multiplanar reformatter 232, and/or the volume renderer 234 may be coupled to an image processor 236 for further enhancement, buffering and temporary storage before being displayed on an image display 238. Optionally, in some embodiments, the image processor 236 may receive I/Q data from the signal processor 226 and/or RF data from the beamformer 222 for enhancement, buffering and temporary storage before being displayed.

According to principles of the present disclosure, in some examples, the image processor 236 may receive imaging data corresponding to image frames of a sequence (e.g., multi-frame loop, cineloop) of contrast enhanced images. Each image frame in the sequence may have been acquired at a different time (e.g., the image frames may be temporally spaced). In some examples, the image processor 236 may perform an adaptive point spread function (PSF) thinning/skeletonization technique (also referred to herein as simply an adaptive thinning technique) on each frame in the sequence. The adaptive thinning technique may be performed on each pixel of each image frame (e.g., the imaging data corresponding to each pixel), including both separable microbubbles and microbubble clusters in some examples. The technique may reshape and/or resize the PSF of the system 200. The size of the adapted PSF may be based, at least in part, on a value of an aggressiveness parameter. The greater the value of the aggressiveness parameter, the smaller the size of the adapted PSF. The lower the value of the aggressiveness parameter, the closer the adapted PSF is to the original PSF of the system 200. The aggressiveness parameter may be adapted in the spatial domain and/or the temporal domain. As will be explained in more detail with reference to FIG. 5, one or more adaptive thinning techniques may be used.

After performing the adaptive thinning technique on all of the images of the sequence, the image processor 236 may perform temporal accumulation in some examples. In other words, the image processor 236 may combine multiple image frames to create the final images of the adaptive CAI image sequence (e.g., high resolution loop), which may include one or more image frames. A variety of techniques may be used. For example, the temporal accumulation step may be performed for the entire sequence (e.g., infinite temporal window) or for a moving window in the temporal domain (e.g., finite temporal window). Techniques for temporal accumulation are described in more detail with reference to FIG. 4. The final adaptive CAI sequence of image frames may be provided to the display 238 and/or local memory 242.

A graphics processor 240 may generate graphic overlays for display with the images. These graphic overlays can contain, e.g., standard identifying information such as patient name, date and time of the image, imaging parameters, and the like. For these purposes the graphics processor may be configured to receive input from the user interface 224, such as a typed patient name or other annotations. The user interface 244 can also be coupled to the multiplanar reformatter 232 for selection and control of a display of multiple multiplanar reformatted (MPR) images.

The system 200 may include local memory 242. Local memory 242 may be implemented as any suitable non-transitory computer readable medium (e.g., flash drive, disk drive). Local memory 242 may store data generated by the system 200 including B-mode images, contrast images, executable instructions, inputs provided by a user via the user interface 224, or any other information necessary for the operation of the system 200.

As mentioned previously, system 200 includes user interface 224. User interface 224 may include display 238 and control panel 252. The display 238 may include a display device implemented using a variety of known display technologies, such as LCD, LED, OLED, or plasma display technology. In some examples, display 238 may comprise multiple displays. The control panel 252 may be configured to receive user inputs (e.g., exam type, time of contrast agent injection). The control panel 252 may include one or more hard controls (e.g., buttons, knobs, dials, encoders, mouse, trackball or others). In some examples, the control panel 252 may additionally or alternatively include soft controls (e.g., GUI control elements or simply, GUI controls) provided on a touch sensitive display. In some examples, display 238 may be a touch sensitive display that includes one or more soft controls of the control panel 252.

According to principles of the present disclosure, in some examples, a user may select an adaptive thinning technique and/or set an aggressiveness parameter to be used for generating the adaptive CAI images via the user interface 224. Adjusting (e.g., varying) the aggressiveness parameter may adjust a final spatial resolution of an adaptive CAI image. In some examples, the user may indicate different aggressiveness parameters for different regions in an image frame and/or indicate how the aggressiveness parameter should change over time. In some examples, the user may select an average or starting aggressiveness parameter to be used and the system 200 adjusts the aggressiveness parameter used spatially over an image frame and/or temporally over multiple image frames. In some examples, the adaptive thinning technique may be pre-set based on exam type, contrast agent type, and/or properties of the image). In some examples, the aggressiveness parameter and/or how it is adjusted spatially and/or temporally may be based on analysis of individual image.

In some examples, various components shown in FIG. 2 may be combined. For instance, image processor 236 and graphics processor 240 may be implemented as a single processor. In another example, the scan converter 230 and multiplanar reformatter 232 may be implemented as a single processor. In some examples, various components shown in FIG. 2 may be implemented as separate components. For example, signal processor 226 may be implemented as separate signal processors for each imaging mode (e.g., B-mode, Doppler). In some examples, one or more of the various processors shown in FIG. 2 may be implemented by general purpose processors and/or microprocessors configured to perform the specified tasks. In some examples, one or more of the various processors may be implemented as application specific circuits. In some examples, one or more of the various processors (e.g., image processor 236) may be implemented with one or more graphical processing units (GPU).

Figure 3:
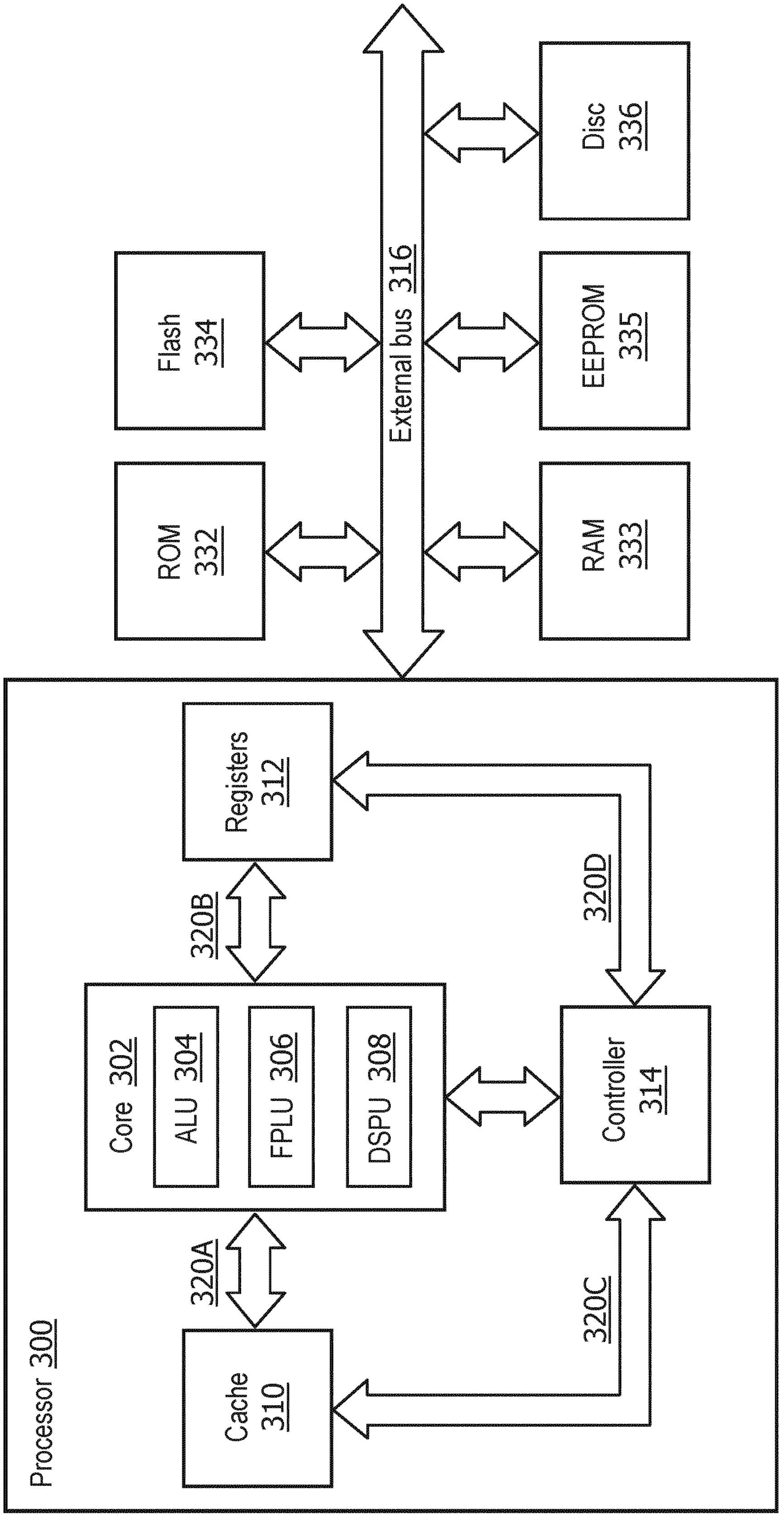
FIG. 3 is a block diagram illustrating an example processor in accordance with some examples of the present disclosure.

FIG. 3 is a block diagram illustrating an example processor 300 according to principles of the present disclosure. Processor 300 may be used to implement one or more processors described herein, for example, image processor 236 shown in FIG. 1. Processor 300 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 300 may include one or more cores 302. The core 302 may include one or more arithmetic logic units (ALU) 304. In some examples, the core 302 may include a floating point logic unit (FPLU) 306 and/or a digital signal processing unit (DSPU) 308 in addition to or instead of the ALU 304.

The processor 300 may include one or more registers 312 communicatively coupled to the core 302. The registers 312 may be implemented using dedicated logic gate circuits (e.g., flip-flops) and/or any memory technology. In some examples the registers 312 may be implemented using static memory. The register may provide data, instructions and addresses to the core 302.

In some examples, processor 300 may include one or more levels of cache memory 310 communicatively coupled to the core 302. The cache memory 310 may provide computer-readable instructions to the core 302 for execution. The cache memory 310 may provide data for processing by the core 302. In some examples, the computer-readable instructions may have been provided to the cache memory 310 by a local memory, for example, local memory attached to the external bus 316. The cache memory 310 may be implemented with any suitable cache memory type, for example, metal-oxide semiconductor (MOS) memory such as static random access memory (SRAM), dynamic random access memory (DRAM), and/or any other suitable memory technology.

The processor 300 may include a controller 314, which may control input to the processor 300 from other processors and/or components included in a system (e.g., control panel 252 and scan converter 230 shown in FIG. 1) and/or outputs from the processor 300 to other processors and/or components included in the system (e.g., display 238 and volume renderer 234 shown in FIG. 1). Controller 314 may control the data paths in the ALU 304, FPLU 306 and/or DSPU 308. Controller 314 may be implemented as one or more state machines, data paths and/or dedicated control logic. The gates of controller 314 may be implemented as standalone gates, FPGA, ASIC or any other suitable technology.

The registers 312 and the cache 310 may communicate with controller 314 and core 302 via internal connections 320A, 320B, 320C and 320D. Internal connections may implemented as a bus, multiplexor, crossbar switch, and/or any other suitable connection technology.

Inputs and outputs for the processor 300 may be provided via a bus 316, which may include one or more conductive lines. The bus 316 may be communicatively coupled to one or more components of processor 300, for example the controller 314, cache 310, and/or register 312. The bus 316 may be coupled to one or more components of the system, such as display 238 and control panel 252 mentioned previously.

The bus 316 may be coupled to one or more external memories. The external memories may include Read Only Memory (ROM) 332. ROM 332 may be a masked ROM, Electronically Programmable Read Only Memory (EPROM) or any other suitable technology. The external memory may include Random Access Memory (RAM) 333. RAM 333 may be a static RANI, battery backed up static RAM, Dynamic RAM (DRAM) or any other suitable technology. The external memory may include Electrically Erasable Programmable Read Only Memory (EEPROM) 335. The external memory may include Flash memory 334. The external memory may include a magnetic storage device such as disc 336. In some examples, the external memories may be included in a system, such as ultrasound imaging system 200 shown in FIG. 2, for example local memory 242.

Figure 4:
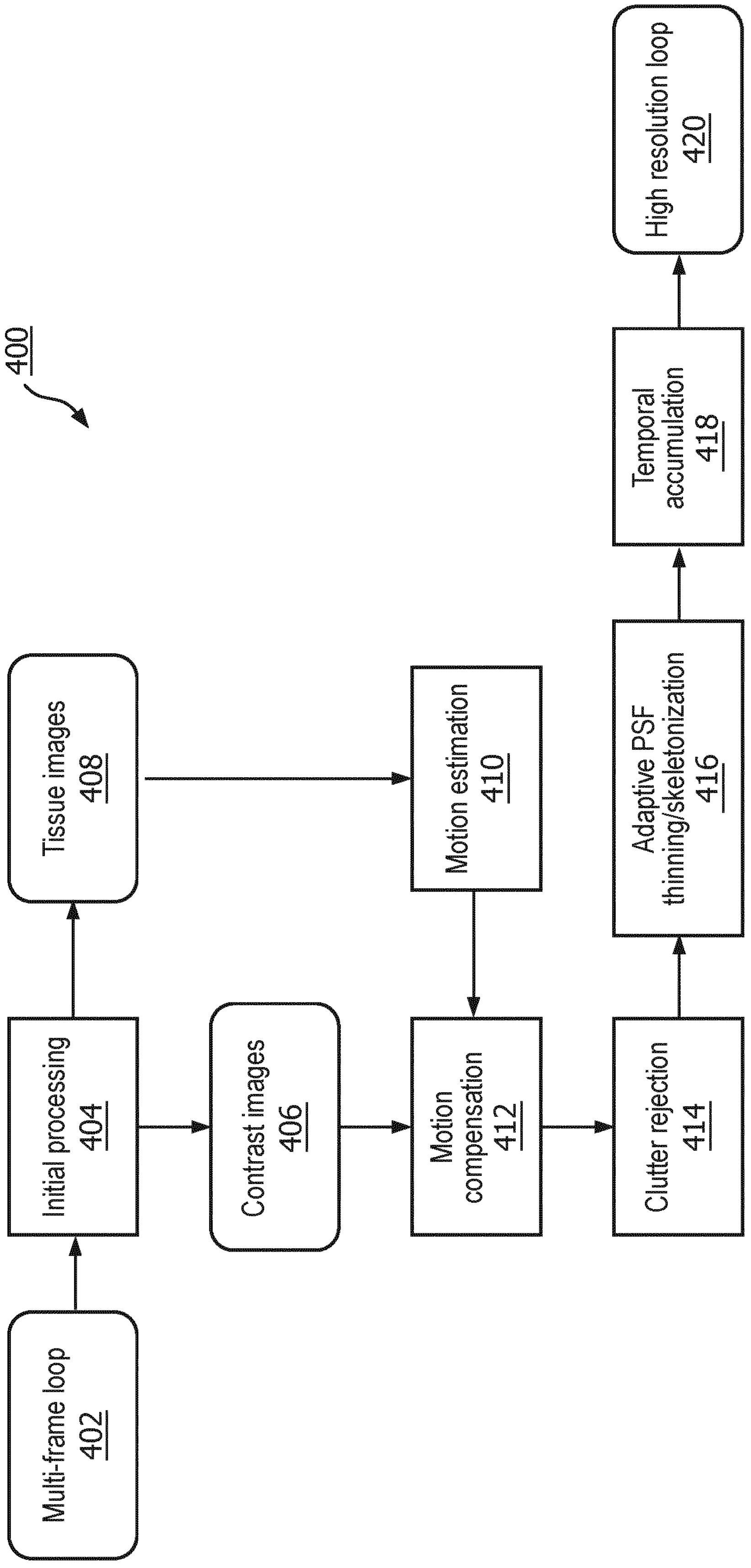
FIG. 4 is a flow chart of a method in accordance with some examples of the present disclosure.

FIG. 4 is a flow chart 400 of a method performed by an image processor, such as image processor 236 shown in FIG. 1, in accordance with examples of the present disclosure.

In some examples, a multi-frame loop (e.g., image sequence) of conventional side-by-side contrast and tissue images may be used as inputs to the signal processor as indicated by block 402. The image format may be DICOM, AVI, WMV, JPEG, and/or other format. The image-domain-based processing may be implemented as an off-line processing feature in some examples. In some applications, the images may be log-compressed with a limited dynamic range, thus, the image-domain implementation of adaptive CAI may have limited performance. In some examples, adaptive CAI may also be implemented at IQ-domain (input is IQ data) or RF-domain (input is RF data) rather than a multi-frame loop as shown in FIG. 4. In some applications, IQ data and/or RF data may provide better performance (e.g., better clutter rejection). In examples using IQ and/or RF data, the image processor may receive data from a signal processor and/or beamformer, such as signal processor 226 and/or beamformer 222 shown in FIG. 1.

At block 404, the image processor may perform image formatting. In some examples, the multi-frame loops are processed to separate the tissue images and contrast images so that they can be processed independently as indicated by blocks 406 and 408. The tissue and contrast images may be properly formatted for following processing blocks. For example, red-green-blue (RGB) images may be converted to gray-scale images (or indexed images) with a desired dynamic range (e.g., normalized from 0 to 1). In some examples, the image processor may receive the tissue images and contrast images from separate imaging streams that do not need to be separated. In examples where enhanced CAI is performed on RF data and/or IQ data rather than a multi-frame loop, image formatting may include separating signals resultant from the contrast agent and signals resultant from the tissue.

At block 410, motion estimation may be performed on the tissue images. Frame-to-frame displacements for each image pixel may be estimated by motion estimation methods, for example, speckle tracking and/or optical flow. Both rigid motion (e.g., translation and rotation) and non-rigid motion (e.g., deformation) may be estimated. Spatial and/or temporal smoothing methods may be applied to the estimated displacements for the tissue images.

At block 412, motion compensation is performed based, at least in part, on the motion estimation performed on the tissue images at block 410. In some examples, tissue images may not be used for motion estimation and the motion estimation techniques discussed above in reference to block 410 may be performed directly on the contrast images. However, in these examples motion compensation may not be as robust.

Optionally, at block 414, clutter rejection filtering may be performed on the contrast images. This may reduce the effect of stationary echoes (especially in the near field), reverbs, etc. Clutter rejection filters can be implemented as finite impulse response (FIR), infinite impulse response (IIR)-based high-pass filters with sufficient numbers of coefficient delay pairs (e.g., taps), a polynomial leastsquares curve fitting filter, and/or singular value decomposition (SVD)-based high-pass filter. Filter parameters may be optimized to suppress most of the residual clutter but preserve most of the contrast signals. In some examples, removal of tissue clutter prior to accumulation may be performed using an adaptive algorithm such as the "TissueSuppress" feature in VM6.0 distributed by Philips™, where nonlinearity differences between tissue and microbubbles are used to mask and then suppress pixels containing tissue on a per-frame basis. In some examples, block 414 may be omitted.

Figure 5:
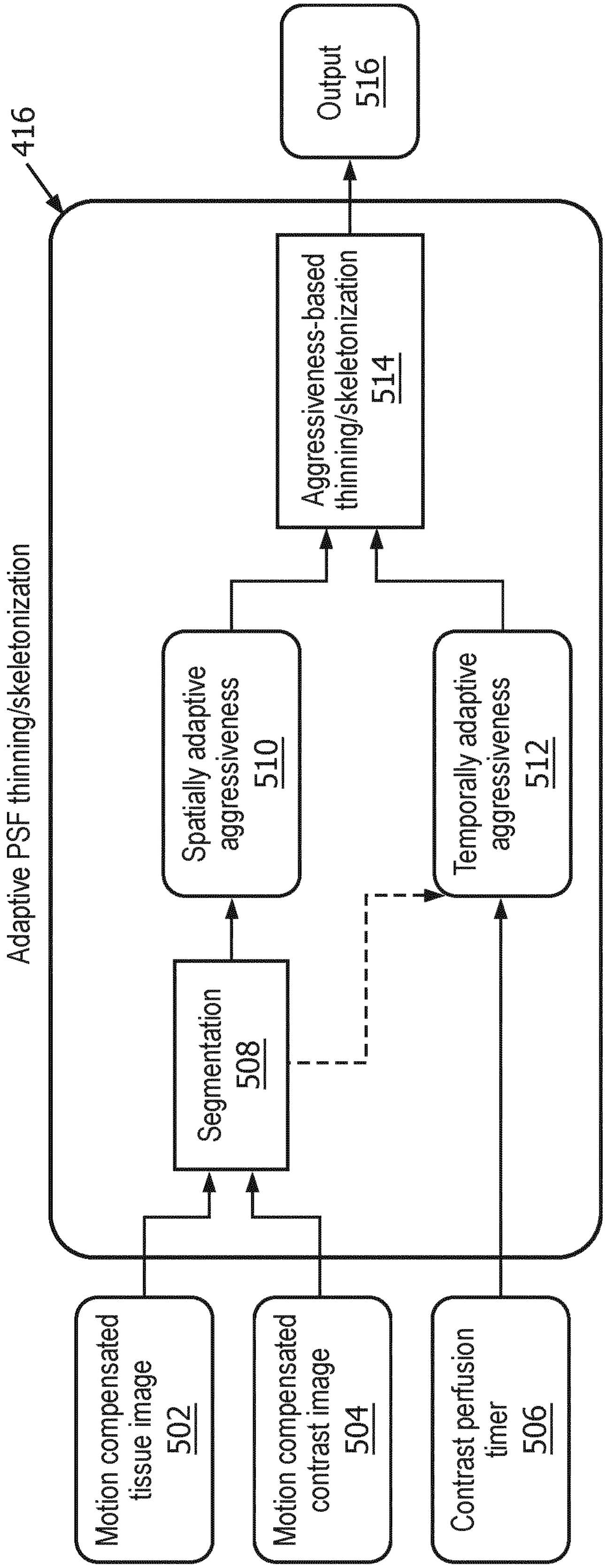
FIG. 5 is a more detailed flow chart of a portion of the method shown in FIG. 4.

After motion compensation (and optionally clutter rejection), an adaptive PSF thinning technique may be performed at block 416. FIG. 5 shows a functional block diagram of the adaptive thinning in accordance with examples of the present disclosure. As shown in FIG. 5, the adaptive thinning technique may receive the motion compensated tissue images (e.g., images generated at block 410), motion compensated contrast images (e.g., images generated at block 412), and timing data from a contrast perfusion timer 506. In some examples, the timing data may be generated based, at least in part, on a user input received via a user interface (e.g., user interface 252) that indicates when the contrast agent was injected.

At block 508, the images from blocks 502 and 504 may be segmented by a suitable image segmenting technique. In some examples, contrast images alone may be used to define different spatial zones with different contrast concentration. In these examples, tissue images may not be segmented. Additionally, temporal (slow-time) filtering can be performed on contrast images to segment out different spatial zones of flow velocities (i.e. blood vessel sizes) based on the slow-time frequencies. Different aggressiveness can be assigned to different zones based on the segmentation, as explained below.

Figure 6A:
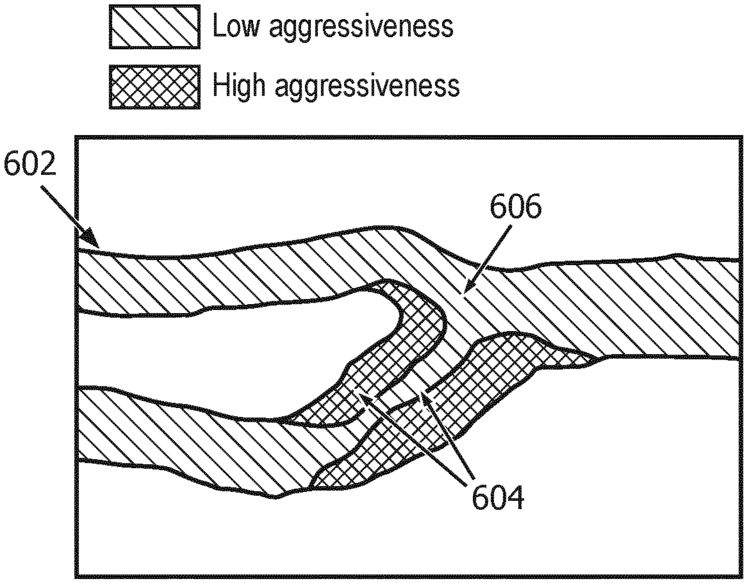
FIG. 6A is an illustration of an example of a spatially adaptive aggressiveness parameter in accordance with some examples of the present disclosure.

At block 510, the segmented images may be analyzed to generate a spatially adaptive aggressiveness parameter. For example, the aggressiveness parameter may be based, at least in part, on blood vessel size. FIG. 6A is an illustration of a carotid artery 602 with plaque 604, which may be imaged using CEUS. In this example, a low aggressiveness (e.g., a low value aggressiveness parameter) may be used for the carotid artery lumen 606 to preserve computational power and a high aggressiveness may be used for the plaque 604 to be able to visualize internal microvasculature of the plaque 604 with high spatial resolution.

In another example for spatially adapting the aggressiveness parameter, the aggressiveness may be based, at least in part, on contrast agent concentration. For example, large vessels may be perfused much earlier than smaller ones. Hence, the concentration of microbubbles will be much higher in the large vessels at early times. A signal intensity threshold value may be set to visualize microvessels with a certain concentration of microbubbles so that large vessels are either masked or their intensity is lowered to enhance smaller vessels. In other words, regions with high signal intensity may be assigned a high value aggressiveness parameter and regions with low signal intensity may be assigned a low value aggressiveness parameter. In other examples, instead of a single threshold value, a function may define how the aggressiveness parameter changes with signal intensity.

Figure 6B:
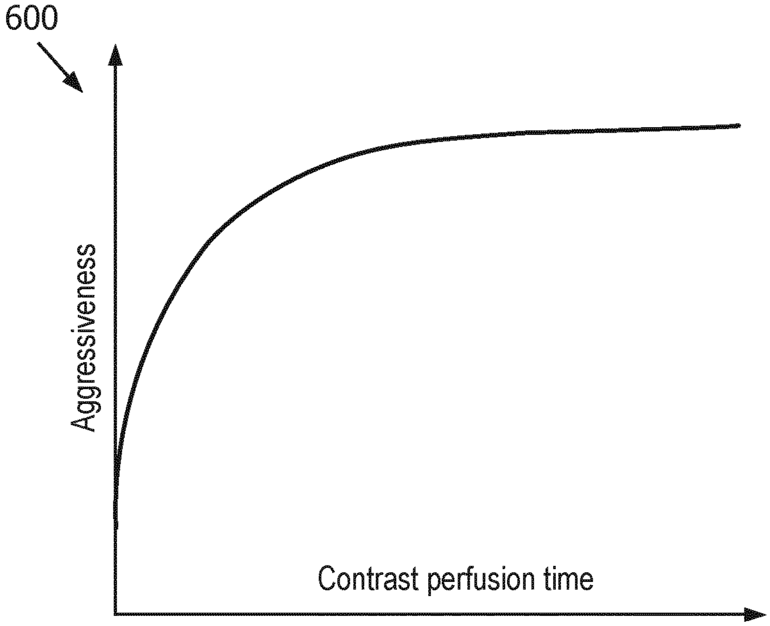
FIG. 6B is an illustration of an example of a temporally adaptive aggressiveness parameter in accordance with some examples of the present disclosure.

Returning to FIG. 5, block 512, the contrast perfusion timing data may be used to generate a temporally adaptive aggressiveness parameter. For example, as shown in the plot 600 of FIG. 6B, the aggressiveness parameter may gradually increase with contrast perfusion time to avoid discontinuous and low sensitivity imaging at the early perfusion phase. In another example, the aggressiveness parameter may be set to a minimum value for a first number of frames (or first time interval), which may be before contrast agent arrives at the imaging region, and the aggressiveness parameter may be ramped up to a higher value after the first number of frames (or after the first time interval) for better resolution of the microbubbles. In some examples, the dynamic range/brightness may also be adjusted based on the aggressiveness to ensure the color map is effective as the aggressiveness parameter changes over time. In some examples, the segmented images may also be analyzed to generate the temporally adaptive aggressiveness parameter.

Although the examples described herein use both spatially and temporally adaptive aggressiveness parameters, in other examples, the aggressiveness parameter may be adaptive in only one of the spatial domain or temporal domain.

Returning to FIG. 5, block 514, the temporally and spatially adaptive aggressiveness parameters are used to perform the adaptive thinning technique on the contrast images. The thinned contrast images are provided as an output at block 516. Any suitable thinning technique may be used with the adaptive aggressiveness parameter(s) to provide an adaptive thinning technique. For example, techniques using morphological operations and techniques using spatial smoothing or low-pass filtering may be used. Several example suitable thinning techniques are provided herein for illustrative purposes, but the principles of the present disclosure are not limited to the examples provided.

In a first example thinning technique, a morphological operation using image erosion may be used. Image erosion may be performed on each frame of the contrast loop to erode away the boundaries of regions and leave shrunken areas of contrast agent signals. Aggressiveness in this example may be a size of a structuring element (e.g., the aggressiveness parameter defines a size of the structuring element). The structuring element may be a shape used to apply functions to the image frame. The shape of the structuring element can be a simple square or rectangle in some examples, but may be more complex shapes in other examples. In this technique, a high aggressiveness parameter (e.g., an aggressiveness parameter having a high value) corresponds to a large size of structuring element. The larger the structuring element, the more boundaries are eroded away, leaving smaller sizes of remaining contrast agent signals. A low aggressiveness parameter (e.g., an aggressiveness parameter having a low value) corresponds to a smaller size of the structuring element and fewer boundaries are eroded away, leaving larger sizes of remaining contrast agent signal areas. The size of the structuring element may be adapted spatially and/or temporally.

In some examples, the image erosion may be grayscale erosion algorithm is applied on each frame of image based on the constructed structuring element. In this technique, the erosion of an image pixel is the minimum of the image pixel in its neighborhood, with that neighborhood defined by the structuring element. The output of the image erosion operation is the output of block 514.

In some examples, the output of the image erosion operation may be referred to as a mask (Mask). The mask may be normalized with values between 0 and 1. A power of an exponent may be applied to the mask. The final output of block 514 (Output) may be the product of the original input (Input) and the normalized mask with the exponent as shown in the equations below:

$$\text{Mask} = \text{Erosion(Input)} \qquad \text{Equation (1)}$$

$$\text{Output} = \text{Input} \times (\text{Normalized Mask})^{\text{Exponent}} \qquad \text{Equation (2)}$$

The exponent (Exponent) may be used to control the aggressiveness parameter in addition to the structuring element. The aggressiveness increases as the exponent increases (e.g., greater than 1).

In a second example thinning technique, a morphological operation using image dilation may be used. In this example, a structuring element, such as the one described in reference to the first example, is also used. Image dilation is provided by the formula:

$$\text{Output} = \frac{\text{Input}}{\text{dilation(Input)}} \qquad \text{Equation (3)}$$

The Output is the output (e.g., thinned) image and the Input is the input image (e.g., the contrast image from block 502). The output image is equal to the input image divided by input image after a dilation operation. Aggressiveness in this example may again be the size of structuring element of image dilation. With high aggressiveness (large size of structuring element), more boundaries are enlarged, leaving smaller regions of remaining contrast agent signals. With low aggressiveness (smaller size of structuring element), less boundaries are enlarged, leaving larger regions of remaining contrast agent signals. The size of the structuring element may be adapted spatially and/or temporally. The dilation technique may be applied to each frame.

In some examples, the image dilation may be a grayscale dilation algorithm. In this algorithm, the dilation of an image pixel is the maximum of the image pixel in its neighborhood, with that neighborhood defined by the structuring element. After the dilation operation, the PSF expands to a larger size depending on the aggressiveness parameter (size of structuring element). The output of this step (each frame of image) is referred as dilation(Input) in Equation 3. The input image may then be scaled based on the dilation output.

According to Equation 3, the input image is scaled with the output of the dilation step. Specifically, each pixel of the output image, output(x, y), is the product of the image pixel, input(x, y), and the corresponding scaling factor, 1/[dilation (input)(x, y)]. Due to the scaling factor, the output PSF shrinks to a smaller size depending on the aggressiveness parameter. Optionally, a normalization step may be applied to the output to remove the outliers (e.g. infinite elements), and normalize the output dynamic range to certain limits.

Figure 7:
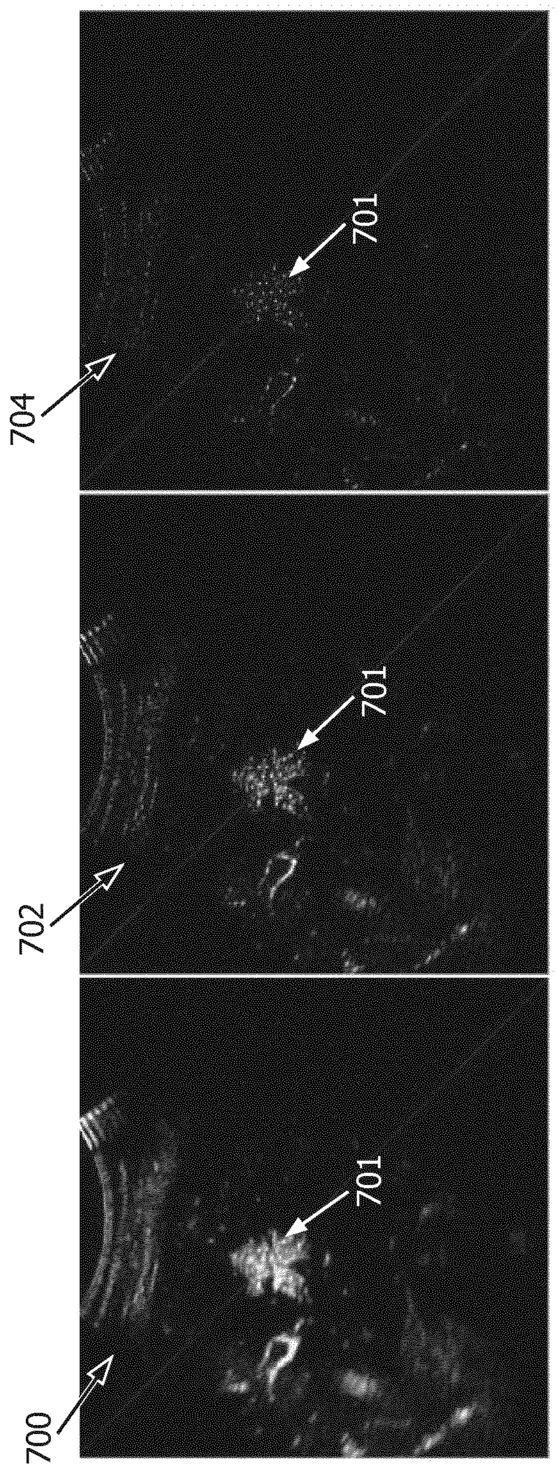
FIG. 7 shows example images with dilation-based thinning with different aggressiveness parameters in accordance with examples of the present disclosure.

Examples of image dilation-based thinning with different aggressiveness parameters (e.g., different sized structuring elements) in accordance with examples of the present disclosure are shown in FIG. 7. Images 700, 702, and 704 are CEUS images of a human liver lesion 701 during the early arterial phase of contrast agent perfusion. Image 700 was obtained by performing image dilation with a low value aggressiveness parameter. The adapted (e.g., adjusted, reshaped) PSF has a slightly smaller size than the original PSF (not shown). Image 702 was obtained by performing image dilation with a medium value aggressiveness parameter. The adapted PSF has a smaller size than the original PSF and the PSF of image 700. Image 704 was obtained by performing image dilation with a high value aggressiveness parameter. The adapted PSF has a much smaller size than the original PSF and the PSF of images 700 and 702.

Similar to the first example describing image erosion, the Output of Equation 3 may be referred to as a mask which may be normalized and raised to an exponent that may be used to control the aggressiveness as described in Equation 2. The final output of block 514 may then be original image multiplied by the normalized mask with the exponent as described in Equation 2.

In a third example, a spatial smoothing thinning technique may be used. The spatial smoothing may be described by the equation:

$$\text{Output} = \frac{\text{Input}}{\text{smoothing(Input)}} \qquad \text{Equation (4)}$$

The Output is the output (e.g., thinned) image and the Input is the input image (e.g., the contrast image from block 502). The output image is equal to the input image divided by input image after spatial smoothing operation. Aggressiveness in this example may be the size of smoothing kernel for spatial smoothing. A high aggressiveness parameter corresponds to a large smoothing kernel size (e.g., 8×8) and more boundaries are smoothed, leaving smaller sizes of remaining contrast signal regions. A low aggressiveness parameter corresponds to a smaller smoothing kernel size (e.g., 3×3) and fewer boundaries are smoothed, leaving larger sizes of remaining contrast signal regions. Generating a smoothing kernel may be similar to generating the structuring element aforementioned. The shape of the smoothing kernel may be a simple square or rectangle in some examples. The size of the smoothing kernel may be adapted temporally and/or spatially.

The output of the spatial smoothing operation, smoothing (input) of Equation 4, may be a result of a 2D spatial convolution between the input image and the smoothing kernel. If the filter coefficient of the smoothing kernel is 1 (e.g., all elements have a value of 1), the spatial smoothing can be simplified as a 2D moving average in some examples. If the filter coefficient of the smoothing kernel is based on certain distribution (e.g. 2D Gaussian distribution), the spatial smoothing may be a weighted moving average. After the smoothing operation, the PSF expands to a larger size depending on the aggressiveness. The output of this step (each frame of image) is referred as smoothing(Input) in Equation 4. The input image may then be scaled based on the smoothing output. According to Equation 4, the input image is scaled with the output of the smoothing step. Specifically, each pixel of the output image, output(x, y), is the product of the image pixel, input(x, y), and the corresponding scaling factor, 1/[smoothing(input)(x, y)]. Due to the scaling factor, the output PSF shrinks to a smaller size depending on the aggressiveness parameter. Optionally, a normalization step may be applied to the output to remove the outliers (e.g. infinite elements), and normalize the output dynamic range to certain limits.

Similar to the examples describing morphological operations, the Output of Equation 4 may be referred to as a mask which may be normalized and raised to an exponent that may be used to control the aggressiveness as described in Equation 2. The final output of block 514 may then be original image multiplied by the normalized mask with the exponent as described in Equation 2.

In a fourth example, a low-pass filter (LPF) thinning technique may be used. The LPF technique may be described by the equation:

$$\text{Output} = \frac{\text{Input}}{LPF(\text{Input})} \qquad \text{Equation (5)}$$

The Output is the output (e.g., thinned) image and the Input is the input image (e.g., the contrast image from block 502). The output image is equal to the input image divided by input image after spatial smoothing operation. Aggressiveness in this example may be the cut-off spatial frequency for spatial LPF. A high aggressiveness parameter corresponds to a lower cut-off frequency and more boundaries are filtered, leaving smaller sizes of remaining contrast signal regions. A low aggressiveness parameter corresponds to a higher cut-off frequency and fewer boundaries are filtered, leaving larger sizes of remaining contrast signal regions. The cut-off frequency may be adapted spatially and/or temporally.

A 2D spatial Fast Fourier Transform (FFT) is performed on the input image. The LPF is then applied to the output of the FFT. This step removes and/or suppresses high spatial frequency components (e.g., the spatial frequency components above the cut-off frequency) of the input image. An inverse FFT is then performed on the filtered image which brings the image from the frequency domain back to the image (e.g., spatial) domain. Because the high frequency components have been removed and/or suppressed, the PSF expands to a larger size depending on the aggressiveness. The output of this step is referred to as LPF(Input) in Equation 5. The input image may then be scaled based on the LPF output. According to Equation 5, the input image is scaled with the output of the LPF step. Specifically, each pixel of the output image, output(x, y), is the product of the image pixel, input(x, y), and the corresponding scaling factor, 1/[LPF(input)(x, y)]. Due to the scaling factor, the output PSF shrinks to a smaller size depending on the aggressiveness parameter. Optionally, a normalization step may be applied to the output to remove the outliers (e.g. infinite elements), and normalize the output dynamic range to certain limits.

Similar to the examples describing morphological operations, the Output of Equation 5 may be referred to as a mask which may be normalized and raised to an exponent that may be used to control the aggressiveness as described in Equation 2. The final output of block 514 may then be original image multiplied by the normalized mask with the exponent as described in Equation 2.

The examples provided herein are for illustrative purposes only and other adaptive thinning techniques may be used. For example, multi-resolution pyramid decomposition, blob-detection, and/or tube-detection image processing techniques may be used. With all of the thinning techniques, the aggressiveness parameters used may vary spatially and/or temporally.

Returning to FIG. 4, at block 418, temporal accumulation (e.g., combining multiple sequential image frames) may be performed on the thinned imaged output from block 416 (e.g., images of block 516 in FIG. 5). In some examples, temporal accumulation may be performed for all of the images in the multi-frame loop to provide an infinite temporal window. In other examples, temporal accumulation may be performed for a moving window at the temporal domain to provide a finite temporal window. The temporal accumulation window (e.g., averaging integration window) may be set not to exceed a certain time interval (e.g., 1 second, 5 seconds, 10 seconds, 30 seconds). The temporal accumulation may provide the final adaptive CAI image sequence, which may be referred to as a high resolution image loop, as indicated by block 420.

Any appropriate temporal accumulation method may be used. Two examples are provided herein for illustrative purposes, but the principles of the present disclosure are not limited to the examples provided. In some examples, a peak-hold or maximum intensity projection method may be used for temporal accumulation. In this method, the final CAI image frame shows only the maximum intensity among all previous input frames at each image pixel. An example MATLAB™ algorithm is provided below for illustration;

```
for k = 1:Nt
  for i = 1:Nz
    for j = 1:Nx
      output(i, j, k) = max(input(i, j, 1:k));
    end
  end
end
```

Input and output loops have the same dimension of [Nz, Nx, Nt], where Nz is the axial dimension, Nx is the lateral dimension, and Nt is the temporal (time) dimension.

In some examples, averaging with exponential correction or average intensity projection may be used. The final CAI image frame shows the temporal average intensity (with exponential correction) among all previous input frames at each image pixel. An example MATLAB™ algorithm is provided below for illustration:

```
for k = 1:Nt
  for i = 1:Nz
    for j = 1:Nx
      output(i, j, k) = mean(input(i, j, 1:k), 3)^expCoef;
    end
  end
end
```

The expCoef is the exponential coefficient to correct the dynamic range of the final sequence of adaptive CAI images (e.g., the output loop), which is typically set to 0.5, but may be adjusted based on the properties of the ultrasound imaging system (e.g., imaging system 100) and/or exam type.

As noted in reference to FIG. 2, in some examples, a user may provide inputs via a user interface (e.g., user interface 252) to select an adaptive thinning technique used and/or have other control over the thinning technique used to generate the final adaptive CAI image sequence. That is, in some examples, the user may have control over the methods described in reference to FIGS. 4 and 5.

In some examples, users may manually control and/or overwrite the aggressiveness parameter of the adaptive PSF thinning/skeletonization step. For example, after processing is complete (e.g., the blocks shown in FIGS. 4-5 have been performed), the users may review the results (e.g., the final CAI image sequence/high resolution loop) with different aggressiveness parameters by manipulating a user control.

In some examples, at the adaptive PSF thinning/skeletonization block 416, multiple levels of adapted aggressiveness parameters may be applied and the results may be stored (e.g., in local memory 242) for the same downstream processing (e.g., block 418). The user may review the results with the different levels of aggressiveness without re-process the datasets. In other examples, instead of calculating different versions of the output loops at multiple aggressiveness levels at block 416, a blending algorithm may be performed between the regular CAI images (e.g., images at block 502) and highly thinned (e.g., high aggressiveness parameter) adaptive CAI images at each pixel and frame. Users can adjust the blending ratio between the two results to achieve the best blending images. In some examples, the original image may be combined with a thinned version of itself based on one or more weights. In some examples, the weights may vary as a function of time. For example, a same thinning operation may be applied to all of the image frames of a sequence (e.g., loop), and the images may contribute to the temporal accumulation process by summing a weight (e.g., a percentage) of the original image with a weight of the thinned image, where the weight may be high (e.g., 90-100%) for a first set of frames and gradually decrease (e.g., down to 10-0%) for subsequent frames.

Figure 8:
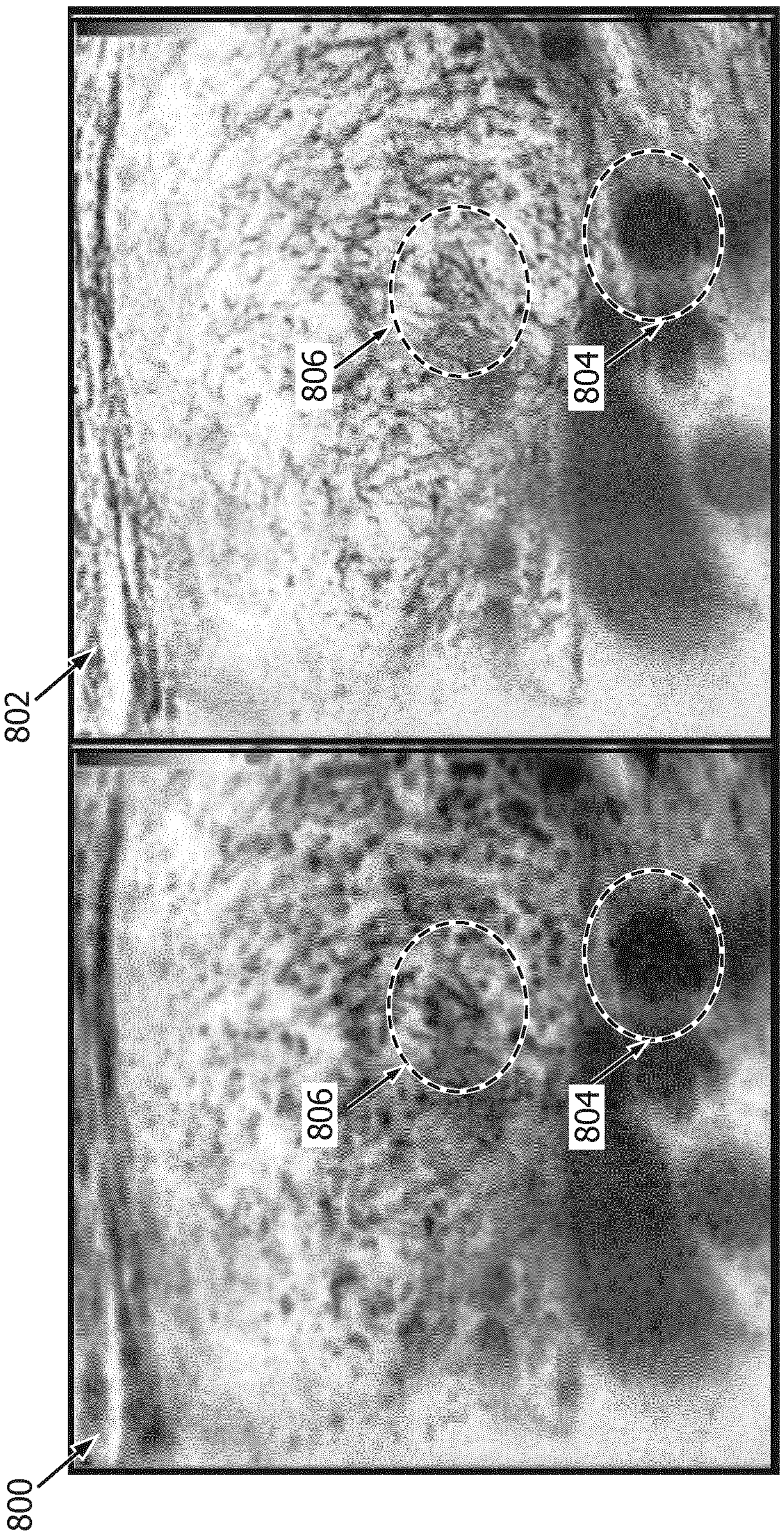
FIG. 8 shows a conventional contrast accumulation imaging image and an adaptive contrast accumulation imaging image in accordance with some examples of the present disclosure.

FIG. 8 shows a conventional CAI image and an adaptive CAI image in accordance with examples of the present disclosure. Images 800 and 802 are CEUS images of a human thyroid. Image 800 was generated using conventional CAI techniques (e.g., combining two or more sequential image frames in a loop). Image 802 was generated using an adaptive thinning technique in accordance with principles of the present disclosure. Image 802 provides better visualization of both larger and smaller areas of perfusion. For example, in region 804, image 800 suffers from saturation and blurring of the perfused area. In image 802, the saturation and blurring are reduced, providing a clearer view of the perfused region 804. In another example, region 806 has blurring in image 800, making it difficult to see the individual vessels. However, in image 802, the microvasculature in region 806 can be more clearly seen.

Figure 9:
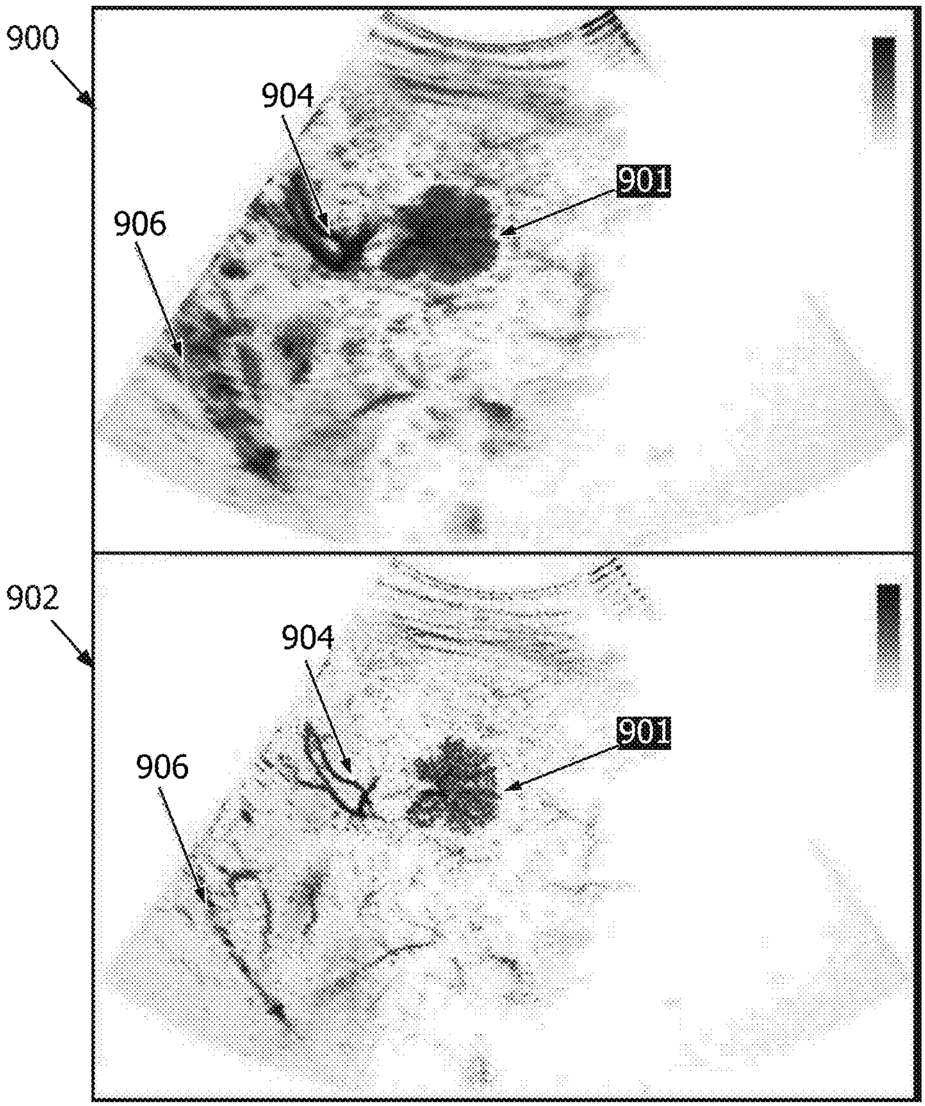
FIG. 9 shows a conventional contrast accumulation imaging image and an adaptive contrast accumulation imaging image in accordance with some examples of the present disclosure.

FIG. 9 shows a conventional CAI image and an adaptive CAI image in accordance with examples of the present disclosure. Images 900 and 902 are CEUS images of a human liver including a lesion 901. Image 900 was generated using conventional CAI techniques (e.g., combining two or more sequential image frames in a loop). Image 902 was generated using an adaptive thinning technique in accordance with principles of the present disclosure. Image 902 provides better visualization of both larger and smaller areas of perfusion. For example, the microvasculature within the lesion 900 may be more clearly discerned in image 902 compared to image 900. In another example, large blood vessels 904 and 906 suffer from significant blurring and saturation in image 900. In image 902, the saturation is reduced and the shapes of the vessels 904 and 906 are more clearly defined.

The systems and methods are described herein for performing adaptive CAI techniques. The adaptive CAI techniques may adapt (e.g., adjust, vary) an aggressiveness parameter of a PSF thinning/skeletonization technique. The aggressiveness parameter may be adapted spatially and/or temporally. Adapting the aggressiveness parameter may allow the adaptive CAI technique to provide improved visualization. The adaptive thinning techniques disclosed herein may allow for improved visualization of both high and low intensity signals within CAI image frames (e.g., areas of high and low perfusion, large and small vessels) in some applications.

In various examples where components, systems and/or methods are implemented using a programmable device, such as a computer-based system or programmable logic, it should be appreciated that the above-described systems and methods can be implemented using any of various known or later developed programming languages, such as "C", "C++ ™", "FORTRAN". "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software, and/or firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instructions to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, examples or processes described herein may be combined with one or more other examples, examples and/or processes or be separated and/or performed amongst separate devices or device portions in accordance with the present systems, devices and methods.

Finally, the above-discussion is intended to be merely illustrative of the present systems and methods and should not be construed as limiting the appended claims to any particular example or group of examples. Thus, while the present system has been described in particular detail with reference to exemplary examples, it should also be appreciated that numerous modifications and alternative examples may be devised by those having ordinary skill in the art without departing from the broader and intended spirit and scope of the present systems and methods as set forth in the claims that follow. Accordingly, the specification and drawings are to be regarded in an illustrative manner and are not intended to limit the scope of the appended claims.

What is claimed is:

1. An ultrasound imaging system comprising:

an ultrasound probe for receiving ultrasound signals for a plurality of contrast-enhanced ultrasound transmit/receive events; and at least one processor in communication with the ultrasound probe, the at least one processor configured to:

perform an adaptive point spread function (PSF) thinning technique on the ultrasound signals for the plurality of transmit/receive events, wherein the adaptive PSF thinning technique is based, at least in part, on an aggressiveness parameter that is adapted in a temporal domain; and temporally accumulate the ultrasound signals for the plurality of transmit/receive events on which the adaptive PSF thinning technique is performed to generate an adaptive contrast accumulation image.

2. The ultrasound imaging system of claim 1, further comprising a beamformer, wherein the ultrasound signals correspond to radio frequency data provided by the beamformer to the at least one processor.

3. The ultrasound imaging system of claim 1, further comprising a signal processor, wherein the ultrasound signals correspond to IQ data provided by the signal processor to the at least one processor.

4. The ultrasound imaging system of claim 1, further comprising a user interface, wherein the user interface is configured to receive a user input that indicates a type of technique to be used as the adaptive PSF thinning technique.

5. The ultrasound imaging system of claim 4, wherein the type of technique is a morphological operation technique.

6. The ultrasound imaging system of claim 4, wherein the type of technique is a spatial smoothing or a low-pass filtering technique.

7. The ultrasound imaging system of claim 1, further comprising a user interface, wherein the user interface is configured to receive a user input that indicates a manner in which the aggressiveness parameter is adapted.

8. The ultrasound imaging system of claim 7, wherein the manner includes applying different values of the aggressiveness parameter in different locations of an image corresponding to the ultrasound signals of at least one of the plurality of transmit/receive events, wherein the image is used to generate the adaptive contrast accumulation image.

9. The ultrasound imaging system of claim 7, wherein the manner includes applying different values of the aggressiveness parameter based, at least in part, on a time at which a contrast agent is injected in a subject from which the ultrasound signals are received.

10. The ultrasound imaging system of claim 1, wherein the aggressiveness parameter is further adapted in a spatial domain.

11. A method comprising:
- receiving a plurality of contrast enhanced ultrasound images;
- performing an adaptive point spread function (PSF) thinning technique on individual images of the plurality of contrast enhanced ultrasound images, wherein the adaptive PSF thinning technique is based, at least in part, on an aggressiveness parameter that is adapted in a temporal domain; and
- temporally accumulating at least two of the individual images of the plurality of contrast enhanced ultrasound images to provide an adaptive contrast accumulation image.

12. The method of claim 11, further comprising:
- receiving a plurality of tissue ultrasound images;
- performing motion estimation on individual ones of the plurality of tissue ultrasound images; and
- performing motion compensation on individual ones of the plurality of contrast enhanced ultrasound images, based at least in part on the motion estimation, prior to performing the adaptive PSF thinning technique.

13. The method of claim 11, further comprising segmenting at least one of the plurality of contrast enhanced ultrasound images to define how the aggressiveness parameter is adapted in the spatial domain.

14. The method of claim 11, further comprising:
- receiving timing data from a contrast perfusion timer; and
- adapting the aggressiveness parameter in the temporal domain based on the timing data.

15. The method of claim 11, wherein the adaptive PSF thinning technique is an image erosion technique, wherein the aggressiveness parameter defines a size of a structuring element of the erosion technique.

16. The method of claim 11, wherein the adaptive PSF thinning technique is an image dilation technique, wherein the aggressiveness parameter defines a size of a structuring element of the dilation technique.

17. The method of claim 11, wherein the adaptive PSF thinning technique is a spatial smoothing technique, wherein the aggressiveness parameter defines a size of a smoothing kernel.

18. The method of claim 11, wherein the adaptive PSF thinning technique is a low-pass filtering technique, wherein the aggressiveness parameter defines a cut-off frequency of a low pass filter.

19. The method of claim 11, wherein temporally accumulating comprises generating a maximum intensity projection.

20. The method of claim 11, wherein temporally accumulating comprises generating an average intensity projection.

21. The method of claim 11, wherein the aggressiveness parameter is further adapted in a spatial domain.

22. A non-transitory, computer-readable medium encoded with executable instructions that when executed cause an ultrasound imaging system to:
- receive a plurality of contrast enhanced ultrasound images;
- perform an adaptive point spread function (PSF) thinning technique on individual ones of the plurality of contrast enhanced ultrasound images, wherein the adaptive PSF thinning technique is based, at least in part, on an aggressiveness parameter that is adapted in a temporal domain; and
- temporally accumulate at least two of the individual ones of the plurality of ultrasound images to provide an adaptive contrast accumulation image.

23. The non-transitory, computer readable medium of claim 22, wherein the aggressiveness parameter is further adapted in a spatial domain.

* * * * *